(12) United States Patent
Berry

(10) Patent No.: US 10,722,380 B1
(45) Date of Patent: Jul. 28, 2020

(54) LATERALLY EXPANDABLE SPINAL IMPLANT

(71) Applicant: Bret Michael Berry, Tallahassee, FL (US)

(72) Inventor: Bret Michael Berry, Tallahassee, FL (US)

( * ) Notice: Subject to any disclaimer, the term of this patent is extended or adjusted under 35 U.S.C. 154(b) by 0 days.

(21) Appl. No.: 16/267,199

(22) Filed: Feb. 4, 2019

(51) Int. Cl.
*A61F 2/44* (2006.01)
*A61F 2/30* (2006.01)

(52) U.S. Cl.
CPC ...... *A61F 2/447* (2013.01); *A61F 2002/3055* (2013.01); *A61F 2002/30523* (2013.01); *A61F 2002/30556* (2013.01); *A61F 2002/30593* (2013.01)

(58) Field of Classification Search
CPC .................. A61F 2/4455; A61F 2/447; A61F 2002/30537–30556; A61F 2002/30576–30579; A61F 2/44
See application file for complete search history.

(56) References Cited

U.S. PATENT DOCUMENTS

| | | | | |
|---|---|---|---|---|
| 5,522,899 A * | 6/1996 | Michelson | ............... | A61F 2/442 606/279 |
| 5,658,335 A * | 8/1997 | Allen | ....................... | A61F 2/44 623/17.16 |
| 6,126,689 A * | 10/2000 | Brett | ..................... | A61F 2/4455 623/17.16 |
| 6,723,126 B1 * | 4/2004 | Berry | .................... | A61F 2/4611 623/17.11 |
| 7,083,650 B2 * | 8/2006 | Moskowitz | ............. | A61F 2/441 606/247 |
| 7,318,839 B2 * | 1/2008 | Malberg | ................ | A61F 2/4455 623/17.11 |
| 7,731,751 B2 * | 6/2010 | Butler | ................ | A61B 17/8858 623/17.11 |
| 8,070,812 B2 * | 12/2011 | Keller | ....................... | A61F 2/44 623/17.11 |
| 8,597,360 B2 * | 12/2013 | McLuen | ............... | A61F 2/4455 623/17.16 |

(Continued)

*Primary Examiner* — Eduardo C Robert
*Assistant Examiner* — Michelle C Eckman
(74) *Attorney, Agent, or Firm* — Ellenoff Grossman & Schole LLP; James M. Smedley; Alex Korona

(57) ABSTRACT

Apparatus and associated methods relate to a laterally expandable spinal implant configured with pivoting wings adapted to secure the implant when inserted between vertebrae with stabilizing force applied to the vertebrae by shaft-driven wedges coupled with the wings. In an illustrative example, the wings may pivot along a hinge axis to swing outward from the implant central body until they press against vertebral endplates superior and inferior. The hinge may be, for example, disposed longitudinally to the implant central body. In some examples, four wings may be mounted axially in the implant central body. Some embodiments may include shaft-driven wedges coupled with the wings and adapted to force the wedges out laterally from the central body. Various examples may advantageously provide improved post-implant spinal stability, enhanced post-implant bone growth, and increased implant contact area with bone, based on the implant pressing the wings against the endplates as the shaft rotates.

20 Claims, 8 Drawing Sheets

(56) References Cited

U.S. PATENT DOCUMENTS

| | | | |
|---|---|---|---|
| 8,795,375 B2* | 8/2014 | Malberg | A61F 2/442 623/17.16 |
| 8,845,733 B2* | 9/2014 | O'Neil | A61F 2/30771 623/17.16 |
| 9,198,765 B1* | 12/2015 | Pimenta | A61F 2/447 |
| 9,381,050 B2* | 7/2016 | Lee | A61B 17/7068 |
| 9,421,112 B2* | 8/2016 | Bal | A61F 2/447 |
| 9,439,771 B2* | 9/2016 | Packer | A61F 2/442 |
| 9,445,918 B1* | 9/2016 | Lin | A61F 2/4601 |
| 9,687,354 B2* | 6/2017 | Bellas | A61F 2/442 |
| 9,913,726 B2* | 3/2018 | Weiman | A61F 2/4455 |
| 10,117,682 B2* | 11/2018 | Wolters | A61B 17/7055 |
| 10,420,654 B2* | 9/2019 | Logan | A61F 2/4455 |
| 10,543,024 B2* | 1/2020 | Lee | A61B 17/7068 |
| 2005/0060036 A1* | 3/2005 | Schultz | A61F 2/44 623/17.15 |
| 2006/0004447 A1* | 1/2006 | Mastrorio | A61B 17/7065 623/17.11 |
| 2006/0142859 A1* | 6/2006 | McLuen | A61F 2/4455 623/17.11 |
| 2007/0198089 A1* | 8/2007 | Moskowitz | A61F 2/442 623/17.11 |
| 2007/0270961 A1* | 11/2007 | Ferguson | A61F 2/44 623/17.11 |
| 2008/0027438 A1* | 1/2008 | Abdou | A61B 17/7062 606/249 |
| 2008/0133014 A1* | 6/2008 | Gately | A61F 2/4425 623/17.16 |
| 2008/0147193 A1* | 6/2008 | Matthis | A61F 2/4425 623/17.16 |
| 2008/0243255 A1* | 10/2008 | Butler | A61F 2/4465 623/17.16 |
| 2009/0054988 A1* | 2/2009 | Hess | A61B 17/025 623/17.16 |
| 2009/0099569 A1* | 4/2009 | Beger | A61F 2/442 606/90 |
| 2009/0234389 A1* | 9/2009 | Chuang | A61B 17/7065 606/249 |
| 2009/0292316 A1* | 11/2009 | Hess | A61B 17/7065 606/249 |
| 2010/0016968 A1* | 1/2010 | Moore | A61B 17/15 623/17.11 |
| 2010/0137989 A1* | 6/2010 | Armstrong | A61F 2/4465 623/17.16 |
| 2010/0286779 A1* | 11/2010 | Thibodeau | A61F 2/442 623/17.11 |
| 2010/0286783 A1* | 11/2010 | Lechmann | A61F 2/3094 623/17.12 |
| 2011/0035011 A1* | 2/2011 | Cain | A61F 2/447 623/17.16 |
| 2011/0178599 A1* | 7/2011 | Brett | A61F 2/4455 623/17.16 |
| 2011/0208311 A1* | 8/2011 | Janowski | A61F 2/4611 623/17.16 |
| 2011/0301712 A1* | 12/2011 | Palmatier | A61F 2/4611 623/17.16 |
| 2011/0319997 A1* | 12/2011 | Glerum | A61F 2/442 623/17.15 |
| 2012/0089185 A1* | 4/2012 | Gabelberger | A61F 2/4405 606/249 |
| 2012/0215316 A1* | 8/2012 | Mohr | A61F 2/442 623/17.16 |
| 2013/0073045 A1* | 3/2013 | Vestgaarden | A61F 2/447 623/17.16 |
| 2013/0079883 A1* | 3/2013 | Butler | A61F 2/4425 623/17.16 |
| 2013/0085572 A1* | 4/2013 | Glerum | A61F 2/44 623/17.16 |
| 2013/0123924 A1* | 5/2013 | Butler | A61B 17/8858 623/17.16 |
| 2013/0184823 A1* | 7/2013 | Malberg | A61F 2/442 623/17.13 |
| 2013/0190876 A1* | 7/2013 | Drochner | A61F 2/442 623/17.16 |
| 2013/0197647 A1* | 8/2013 | Wolters | A61F 2/446 623/17.16 |
| 2013/0261747 A1* | 10/2013 | Geisert | A61F 2/442 623/17.16 |
| 2013/0325128 A1* | 12/2013 | Perloff | A61F 2/447 623/17.16 |
| 2013/0340240 A1* | 12/2013 | Irawan | A61B 17/7258 29/525.11 |
| 2014/0012383 A1* | 1/2014 | Triplett | A61F 2/4465 623/17.16 |
| 2014/0018922 A1* | 1/2014 | Marino | A61F 2/447 623/17.16 |
| 2014/0031938 A1* | 1/2014 | Lechmann | A61F 2/4425 623/17.16 |
| 2014/0039622 A1* | 2/2014 | Glerum | A61F 2/28 623/17.15 |
| 2014/0094916 A1* | 4/2014 | Glerum | A61F 2/442 623/17.15 |
| 2014/0128977 A1* | 5/2014 | Glerum | A61F 2/447 623/17.16 |
| 2014/0172106 A1* | 6/2014 | To | A61F 2/442 623/17.16 |
| 2014/0180421 A1* | 6/2014 | Glerum | A61F 2/30771 623/17.16 |
| 2014/0194992 A1* | 7/2014 | Medina | A61F 2/4611 623/17.16 |
| 2014/0277490 A1* | 9/2014 | Perloff | A61F 2/4455 623/17.16 |
| 2014/0336764 A1* | 11/2014 | Masson | A61F 2/4455 623/17.15 |
| 2014/0364951 A1* | 12/2014 | De Villiers | A61F 2/4611 623/17.16 |
| 2015/0073552 A1* | 3/2015 | To | A61F 2/4611 623/17.15 |
| 2015/0100128 A1* | 4/2015 | Glerum | A61F 2/447 623/17.16 |
| 2015/0148908 A1* | 5/2015 | Marino | A61F 2/30771 623/17.16 |
| 2015/0209152 A1* | 7/2015 | Patterson | A61F 2/447 623/17.13 |
| 2015/0366675 A1* | 12/2015 | Matthews | A61F 2/30771 623/17.16 |
| 2015/0374507 A1* | 12/2015 | Wolters | A61B 17/8858 623/17.15 |
| 2016/0038305 A1* | 2/2016 | Weiman | A61F 2/447 623/17.16 |
| 2016/0058565 A1* | 3/2016 | Zappacosta | A61F 2/4455 623/17.16 |
| 2016/0166396 A1* | 6/2016 | McClintock | A61F 2/30771 623/17.16 |
| 2016/0206439 A1* | 7/2016 | To | A61F 2/442 |
| 2017/0000622 A1* | 1/2017 | Thommen | A61F 2/4425 |
| 2017/0056200 A1* | 3/2017 | Koch | A61F 2/4455 |
| 2017/0056201 A1* | 3/2017 | Liang | A61F 2/447 |
| 2017/0065423 A1* | 3/2017 | Lauf | A61F 2/4202 |
| 2017/0209282 A1* | 7/2017 | Aghayev | A61F 2/4455 |
| 2017/0231778 A1* | 8/2017 | Overes | A61F 2/4465 623/17.16 |
| 2017/0312090 A1* | 11/2017 | Sharabani | A61F 2/447 |
| 2017/0312092 A1* | 11/2017 | Link | A61F 2/4684 |
| 2017/0325965 A1* | 11/2017 | Kim | A61F 2/44 |
| 2017/0325967 A1* | 11/2017 | Link | A61F 2/4455 |
| 2018/0000606 A1* | 1/2018 | Hessler | A61F 2/447 |
| 2018/0000609 A1* | 1/2018 | Hessler | A61F 2/447 |
| 2018/0078384 A1* | 3/2018 | Suddaby | A61F 2/446 |
| 2018/0098860 A1* | 4/2018 | To | A61F 2/4465 |
| 2018/0110629 A1* | 4/2018 | Ewer | A61F 2/4455 |
| 2018/0116811 A1* | 5/2018 | Bernard | A61F 2/4455 |
| 2018/0116812 A1* | 5/2018 | Bernard | A61F 2/4455 |
| 2018/0116816 A1* | 5/2018 | Weiman | A61F 2/442 |
| 2018/0116817 A1* | 5/2018 | Weiman | A61F 2/44 |
| 2018/0125671 A1* | 5/2018 | Bernard | A61F 2/4611 |
| 2018/0193164 A1* | 7/2018 | Shoshtaev | A61F 2/4611 |
| 2019/0021873 A1* | 1/2019 | Dmuschewsky | A61F 2/4425 |
| 2019/0224017 A1* | 7/2019 | Grim | A61F 2/442 |

(56) References Cited

U.S. PATENT DOCUMENTS

2019/0269521 A1\* 9/2019 Shoshtaev .............. A61F 2/447
2019/0274838 A1\* 9/2019 Manwill ................. A61F 2/447
2019/0290448 A1\* 9/2019 Predick ................. A61F 2/4611
2019/0321198 A1\* 10/2019 Glerum ................. A61F 2/4611

\* cited by examiner

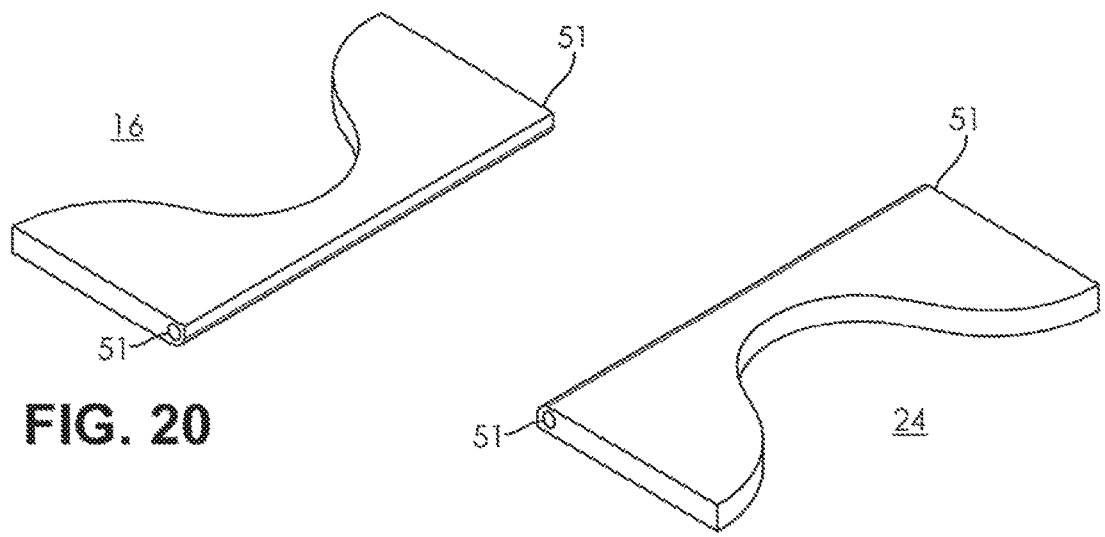
FIG. 20
FIG. 21
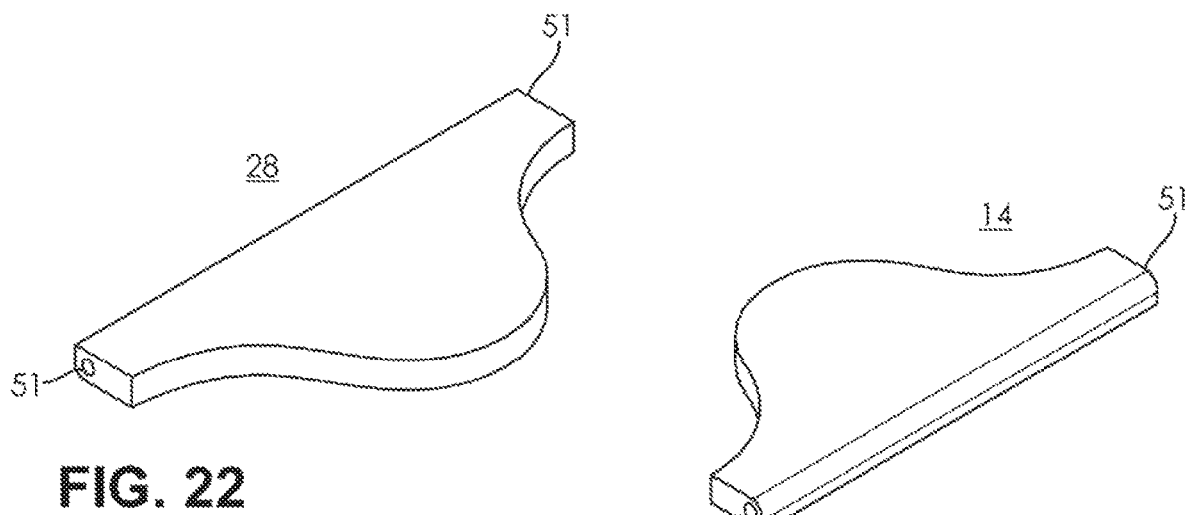
FIG. 22
FIG. 23

LATERALLY EXPANDABLE SPINAL IMPLANT

TECHNICAL FIELD

Various embodiments relate generally to spinal implants.

BACKGROUND

Spinal implants are devices that may be implanted within a spine. Some spinal implants may be surgically inserted within the spine. For example, some spinal implants may be inserted between vertebrae during spinal surgery. Spinal surgery may be performed to alleviate back pain. In some cases, back pain may be severe, and even debilitating. In some scenarios, a medical patient's back pain may be due to damage, disease, or inflammation affecting the vertebrae or intervertebral discs. For example, disabling back pain may arise from disruption of the disc annulus. In some examples, back pain may be a result of instability of the vertebral bodies surrounding a damaged intervertebral disc.

In some cases of severe back pain, mechanical limitation to the movement of vertebrae may be advantageous. In some scenarios, treatment for back pain may require surgical disc removal. For example, damage to intervertebral disc tissue may require surgical removal of the disc nucleus. In some cases, instability of the vertebral bodies that surrounded the removed disc may result. In an illustrative example, persistent inflammation or instability due to a removed disc may result in a recurrence of disabling back pain after surgery. In some cases, the likelihood of back pain recurring after disc removal may be reduced and back pain recurrence mitigated by stabilization of the adjacent vertebral bodies subsequent to disc removal. For example, vertebrae adjacent to the removed disc may be surgically fused with the aid of a fusion device implanted between vertebrae.

Some spinal implant surgery may have time-limited benefits. For example, some spinal implants may subside into the vertebral endplates as time passes after fusion surgery. In some examples, spinal implant subsidence into the vertebral endplates may be a result of limited contact area between the implant and endplates. In an illustrative example, spinal implant subsidence into the adjacent vertebral endplates may result in back pain due to reduced spacing between the vertebral bodies. Some spinal implants limit the vertebral endplate surface area in contact with the implant, which may limit bone growth. Limited bone growth between the fused vertebrae after implantation may result in limited spinal stability. Some spinal implants may be composed from multiple separate components that must be individually assembled together within the intervertebral disc space, making optimal placement of the spinal implant difficult in some scenarios.

SUMMARY

Apparatus and associated methods relate to a laterally expandable spinal implant configured with pivoting wings adapted to secure the implant when inserted between vertebrae with stabilizing force applied to the vertebrae by shaft-driven wedges coupled with the wings. In an illustrative example, the wings may pivot along a hinge axis to swing outward from the implant central body until they press against vertebral endplates superior and inferior. The hinge may be, for example, disposed longitudinally to the implant central body. In some examples, four wings may be mounted axially in the implant central body. Some embodiments may include shaft-driven wedges coupled with the wings and adapted to force the wedges out laterally from the central body. Various examples may advantageously provide improved post-implant spinal stability, enhanced post-implant bone growth, and increased implant contact area with bone, based on the implant pressing the wings against the endplates as the shaft rotates.

Various embodiments may achieve one or more advantages. For example, some embodiments may improve positive spinal fusion outcome rates. This facilitation may be a result of reducing the load per unit area placed against vertebral bodies by the implant, based on securing the implant with pivoting wings shaped to align with the vertebral endplate surfaces. In some embodiments, the effective period of a patient's relief from back pain after fusion surgery may be extended. Such extended patient pain relief from back pain after fusion surgery may be a result of increased contact surface area between the implant and vertebral endplates. For example, increased contact surface area between the implant and vertebral endplates may reduce implant subsidence into the vertebral endplates, enhancing spinal stability. Some embodiments may improve fusion bone growth after spinal implant surgery. Such increased bone growth between vertebrae after fusion may be a result of securely fixing the implant to the vertebral bodies during surgery. For example, preventing movement between the implant and vertebral bodies may result in improved bone growth and more successful fusion of the vertebrae.

Some embodiments may reduce the effort required in implant surgery. Such reduced surgical implantation effort may result from a spinal implant configured to laterally expand in place based on pivoting wings adapted to secure the implant when inserted between vertebrae with stabilizing force applied to the vertebrae by shaft-driven wedges coupled with the wings. For example, such a spinal implant laterally expandable in place may be more easily used in even tightly constrained surgical cavities. Some embodiments may improve access to spinal fusion surgery. Such improved access to reduced back pain may be a result of expanding the amount of bone graft material that may be used with the implant. For example, increasing the contact surface area between the implant wings and the vertebral endplates may increase the graft material area able to contact the endplates, which may increase the likelihood of solid bone growth between the vertebrae.

The details of various embodiments are set forth in the accompanying drawings and the description below. Other features and advantages will be apparent from the description and drawings, and from the claims.

BRIEF DESCRIPTION OF THE DRAWINGS

FIG. 20 depicts a perspective view of an exemplary spinal implant wing.

FIG. 21 depicts a perspective view of an exemplary spinal implant wing.

FIG. 22 depicts a perspective view of an exemplary spinal implant wing.

FIG. 23 depicts a perspective view of an exemplary spinal implant wing.

Like reference symbols in the various drawings indicate like elements.

DETAILED DESCRIPTION OF ILLUSTRATIVE EMBODIMENTS

To aid understanding, this document is organized as follows. First, illustrative usage of an exemplary laterally expandable spinal implant configured with pivoting wings adapted to secure the implant when inserted between vertebrae with stabilizing force applied to the vertebrae by shaft-driven wedges coupled with the wings is briefly introduced with reference to FIG. 1. Second, with reference to FIGS. 2-15, the discussion turns to exemplary embodiments that illustrate the design and operation of an exemplary laterally expandable spinal implant. Specifically, views of an exemplary laterally expandable spinal implant depicted in various illustrative configurations are disclosed. Finally, with reference to FIGS. 16-23, illustrative designs of exemplary laterally expandable spinal implant component parts are disclosed.

Figure 1:
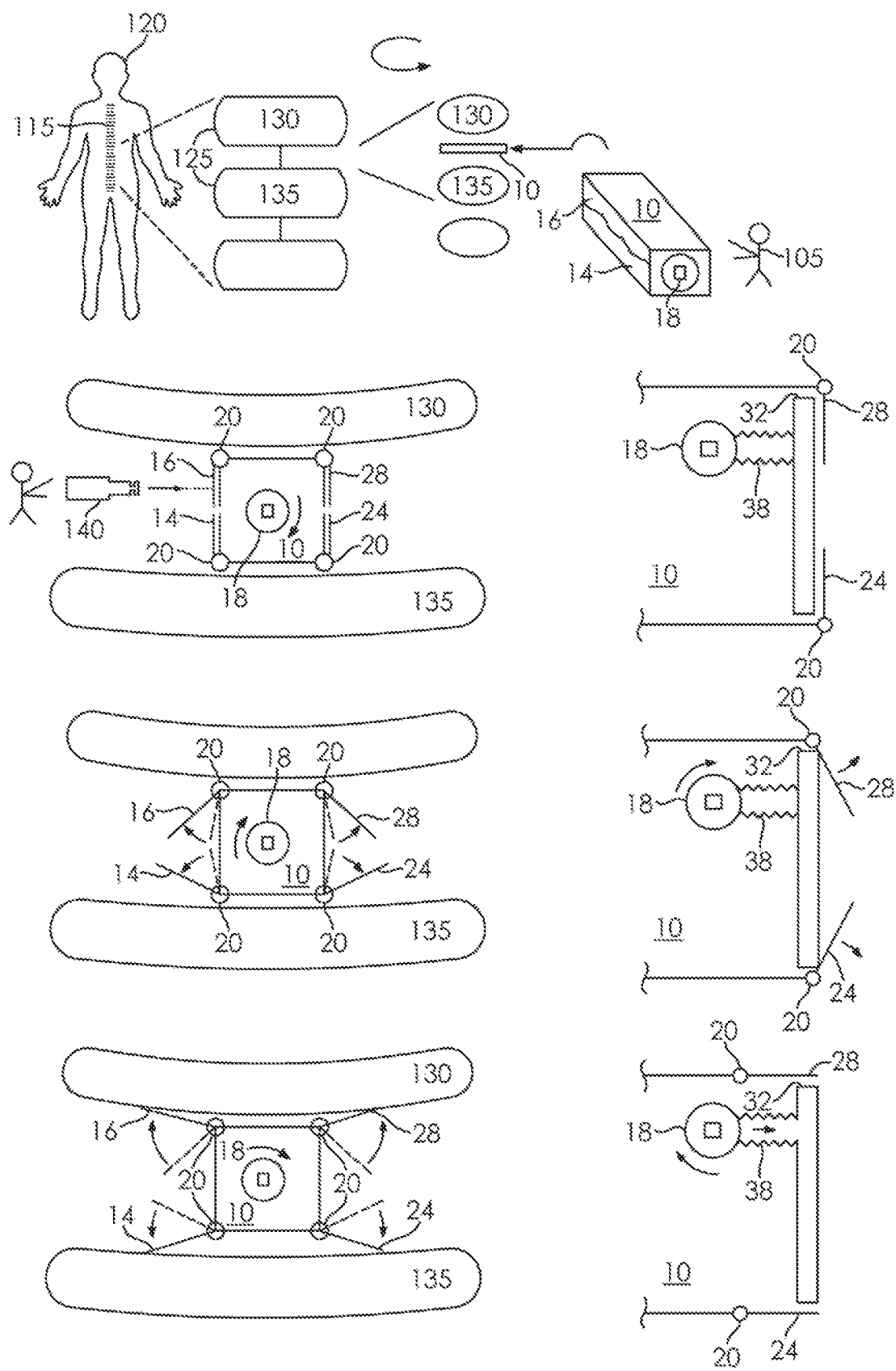
FIG. 1 depicts an operational view of an exemplary laterally expandable spinal implant configured with pivoting wings adapted to secure the implant when inserted between vertebrae with stabilizing force applied to the vertebrae by shaft-driven wedges coupled with the wings.

FIG. 1 depicts an operational view of an exemplary laterally expandable spinal implant configured with pivoting wings adapted to secure the implant when inserted between vertebrae with stabilizing force applied to the vertebrae by shaft-driven wedges coupled with the wings. In FIG. 1, the surgeon 105 inserts the spinal implant 10 within the spine 115 of the patient 120. In the depicted example, the spinal implant 10 is inserted between the pair of vertebrae 125. In the illustrated example, the spinal implant 10 is inserted between superior vertebral endplate 130 and inferior vertebral endplate 135 of the pair of vertebrae 125. In the illustrated example, the surgeon 105 rotationally drives spinal implant 10 drive shaft 18 with spinal implant installation tool 140. In the depicted embodiment, the spinal implant 10 drive shaft 18 rotational action expands wings 16, 28, 14, and 24 outward from the spinal implant 10 to secure the spinal implant 10 with stabilizing force applied to the pair of vertebrae 125 by the wings 16, 28, 14, and 24. In the illustrated embodiment, each of the wings 16, 28, 14, and 24 pivots along a longitudinal hinge axis of the spinal implant 110. In the depicted embodiment, each of the wings 16, 28, 14, and 24 are rotationally coupled with the spinal implant 10 by hinge pin 20 pair. In the illustrated embodiment, the wings 16 and 14 are in mechanical contact with wedge 26, depicted in FIGS. 3, 4, 5, 6, 7, 8, 9, 15, and 19. In the depicted embodiment, the wings 28 and 24 are in mechanical contact with wedge 32. In the depicted embodiment, the wedges 26 and 32 are slidably coupled with the drive shaft 18. In the illustrated embodiment, the wedges 26 and 32 are configured to force the wings 16, 28, 14, and 24 outward from the spinal implant 10 to secure the implant with a stabilizing force applied to the pair of vertebrae 125 by the wings 16, 28, 14, and 24 when sufficient rotational force is applied to the drive shaft 18.

Figure 2:
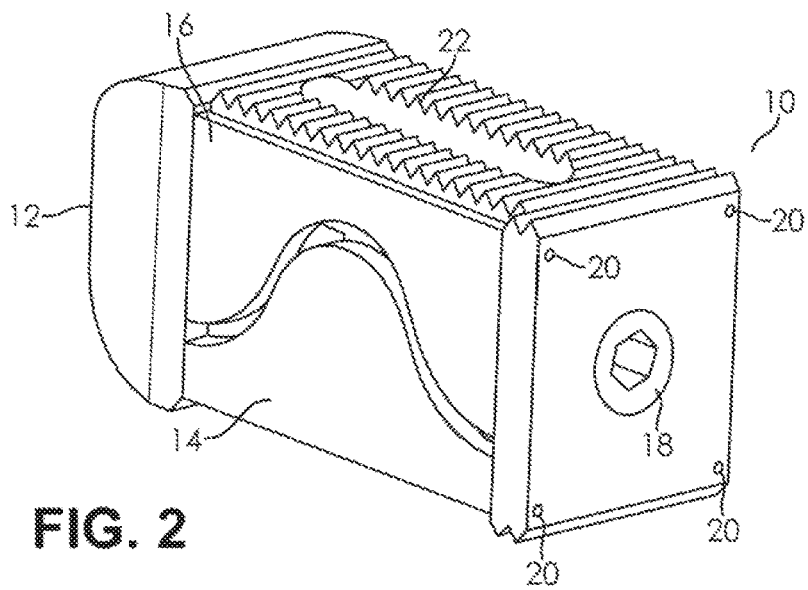
FIG. 2 depicts a top, rear perspective view of an exemplary spinal implant in an illustrative unexpanded configuration.

FIG. 2 depicts a top, rear perspective view of an exemplary spinal implant in an illustrative unexpanded configuration. In FIG. 2, the spinal implant 10 includes central body 12 configured with four wings 14, 16, 24, 28. In the depicted embodiment, each wing 14, 16, 24, 28 is rotationally coupled with the central body 12 by hinge pin 20 pair. In the illustrated embodiment, each wing 14, 16, 24, 28 is allowed to mesh with an opposing wing which is attached to the same side of the central body 12. For example, the lower left wing 14 is long in the its center, while the upper left wing 16 is narrow in the center and long at its ends. This allows both wings 14 and 16 to nest within the central body 12 while in the unexpanded form. Lower right wing 24 and upper right wing 28, depicted in FIG. 1, are configured in a manner similar to wings 14 and 16, to mesh with an opposing wing which is attached to the same side of the central body 12. For example, the lower right wing 24 is narrow in the its center, while the upper left wing 28 is long in the center and narrow at its ends. This allows both wings 24 and 28 to nest within the central body 12 while in the unexpanded form. In the illustrated embodiment, the wings 14, 16, 24, 28 are held in place within the central body 12 in the unexpanded form by a simple interference fit.

Figure 3:
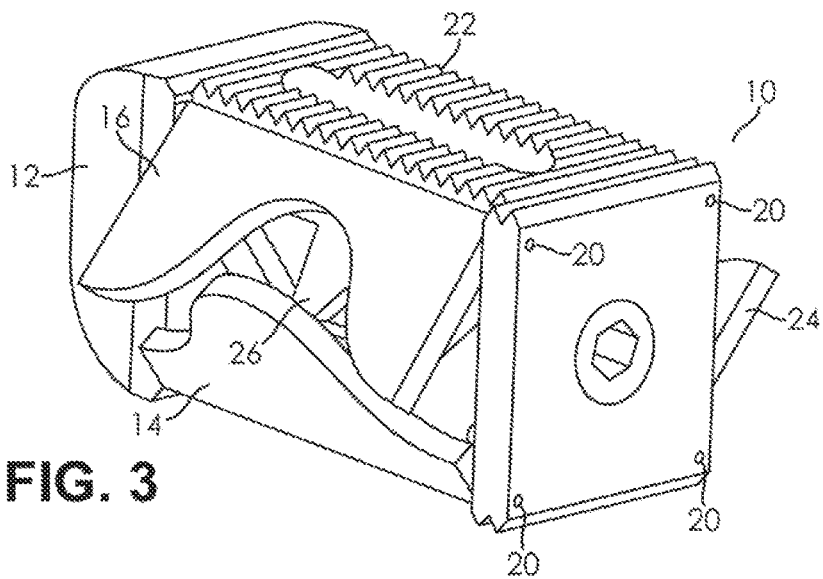
FIG. 3 depicts a top, rear perspective view of an exemplary spinal implant in an illustrative first partially expanded configuration.

FIG. 3 depicts a top, rear perspective view of an exemplary spinal implant in an illustrative first partially expanded configuration. In FIG. 3, the drive shaft 18 has turned, laterally displacing the wedge 26 outward from the spinal implant 10 central body 12. In the depicted embodiment, the displacement of the wedge 26 outward from the spinal implant 10 central body 12 drives upper left wing 16 and lower left wing 14 to pivot on hinge pin 20 pairs along axes longitudinal to the central body 12. In the illustrated embodiment, the spinal implant 10 central body 12 is defined by cavities opening from central body 12 lateral faces. In the depicted embodiment, the cavities opening from central body 12 lateral faces are configured to house the wings 14, 16, 24, 28 when the spinal implant 10 is in an unexpanded configuration. In the illustrated embodiment, the spinal implant 10 central body 12 has teeth 22 on both its superior and inferior faces. In the depicted embodiment, a cylindrical cavity is centrally located along the longitudinal axis of the spinal implant 10 central body 12. In the illustrated embodiment, the spinal implant 10 drive shaft 18 is rotatably retained within the cylindrical cavity. In the depicted embodiment, the spinal implant 10 cylindrical cavity extends from the posterior wall of the spinal implant 10 central body 12 into the nose of the spinal implant 10 central body 12. In the illustrated embodiment, the spinal implant 10 drive shaft 18 includes a gear 40, depicted in FIGS. 6, 7, 8, 9, 17, disposed along at least a portion of the drive shaft 18. In the depicted embodiment, the spinal implant 10 drive shaft 18 can spin within the central body 12 cylindrical cavity, turning the gear 40.

Figure 4:
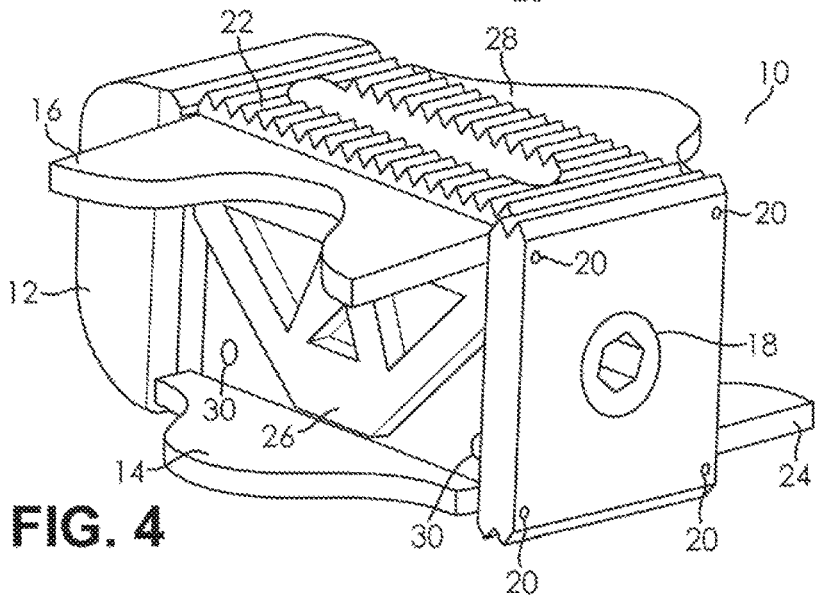
FIG. 4 depicts a top, rear perspective view of an exemplary spinal implant in an illustrative second partially expanded configuration.

FIG. 4 depicts a top, rear perspective view of an exemplary spinal implant in an illustrative second partially expanded configuration. In FIG. 4, spinal implant 10 central body 12 cavities house left wedge 26 and right wedge 32, depicted in FIGS. 1, 5, 6, 7, 8, and 18, when the spinal implant 10 is in an unexpanded configuration. In the illustrated embodiment, the lower left wing 14 and the upper left wing 16 are depicted pivoted outward from the spinal implant 10 central body 12 in a partially expanded configuration. In the depicted embodiment, the lower left wing 14 and upper left wing 16 are in mechanical contact with the left wedge 26. In the depicted embodiment, the left wedge 26 is slidably coupled with the spinal implant 10. In the illustrated embodiment, the drive shaft 18 rotationally engages the left wedge 26 to drive the wedge with a sliding action outward from the spinal implant 10 central body 12 as the drive shaft 18 is rotated. In the illustrated embodiment, the spinal implant 10 drive shaft 18 has turned, laterally displacing with a sliding action the left wedge 26 outward from the spinal implant 10 central body 12. In the depicted embodiment, the sliding action of the left wedge 26 outward from the central body 12 drives the upper left wing 16 and lower left wing 14 to swing with a pivoting action outward from the central body 12. In the illustrated embodiment, right wedge 32, depicted in FIGS. 1, 5, 6, 7, 8, and 18, is slidably coupled with the spinal implant 10 drive shaft 18. In the illustrated embodiment, the drive shaft 18 rotationally engages right wedge 32 to drive the wedge with a sliding action outward from the spinal implant 10 central body 12 when the drive shaft 18 is rotated. In the illustrated embodiment, the spinal implant 10 drive shaft 18 has turned, slidably displacing the right wedge 32 outward from the spinal implant 10 central body 12. In the depicted embodiment, the sliding action of the right wedge 32 outward from the central body 12 drives the upper right wing 28 and lower right wing 24 to swing with a pivoting action outward from the central body 12.

Figure 5:
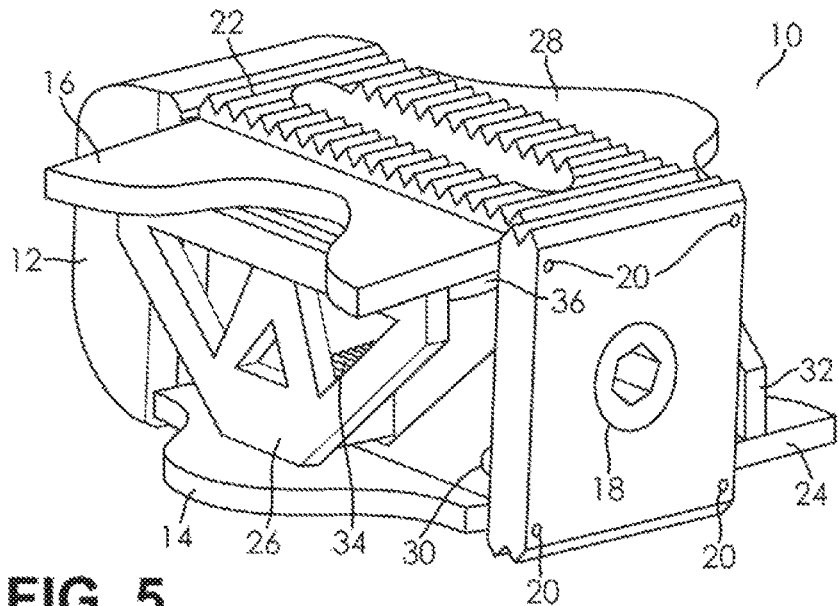
FIG. 5 depicts a top, rear perspective view of an exemplary spinal implant in an illustrative expanded configuration.

FIG. 5 depicts a top, rear perspective view of an exemplary spinal implant in an illustrative expanded configuration. In FIG. 5, the cavities opening from central body 12 lateral faces are configured to house the wedges 26, 32 when the spinal implant 10 is in an unexpanded configuration. In the depicted embodiment, the left wedge 26 has two guide protrusions 36 that act to align it within the central body 12. In the illustrated embodiment, the guide protrusions 36 slide within guide holes 30 on the central body 12. In the depicted embodiment, the guide protrusions 36 are transverse to the body of the wedge 26. In the illustrated embodiment, the right wedge 32 has two protrusions 42, depicted in FIGS. 7, 8, 15, and 18, that act to align it within the central body 12. In the depicted embodiment, the guide protrusions 42 slide within guide holes 30 on the central body 12. In the illustrated embodiment, the guide protrusions 42 are transverse to the body of the right wedge 32. In the depicted embodiment, the left wedge 26 includes left rack protrusion 34. In the illustrated embodiment, the right wedge 32 includes right rack protrusion 38. In the depicted embodiment, left rack protrusion 34 extends transverse to the body of the left wedge 26. In the illustrated embodiment, right rack protrusion 28 extends transverse to the body of the right wedge 32. In the depicted embodiment, the left rack protrusion 34 extends into the inferior portion of the central body 12 and across the gear 40. In the illustrated embodiment, the right rack protrusion 38 extends into the superior portion of the central body 12 and across the gear 40.

Figure 6:
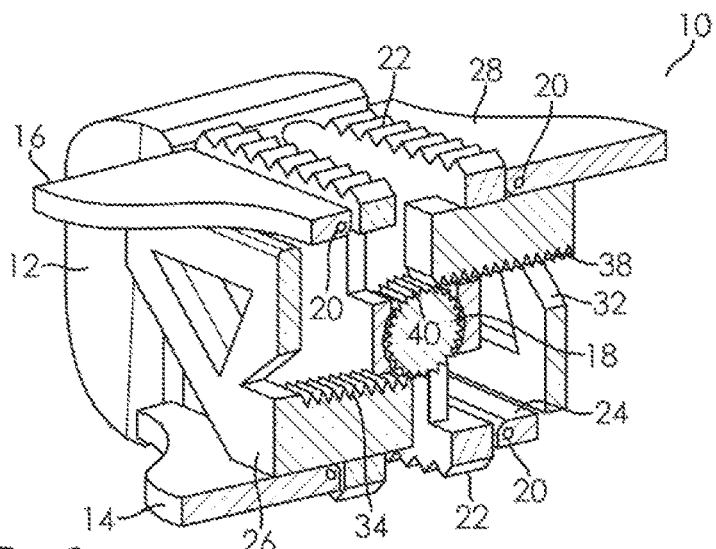
FIG. 6 depicts a top, rear, perspective sectional view of an exemplary spinal implant in an illustrative expanded configuration.

FIG. 6 depicts a top, rear, perspective sectional view of an exemplary spinal implant in an illustrative expanded configuration. In FIG. 6, the implant 10 was inserted between two vertebrae while in an unexpanded configuration, and the drive shaft 18 turned, as depicted in FIG. 1. In some embodiments, insertion of the spinal implant 10 between vertebrae while the spinal implant 10 is in an unexpanded configuration minimizes dissection of bone and tissue, and allows minimal disruption of neural elements. In the illustrated embodiment, the drive shaft 18 clockwise rotation has turned the gear 40. In the depicted embodiment, the gear 40 engages both the left rack protrusion 34 and the right rack protrusion 38 simultaneously. In the illustrated embodiment, the gear 40 drives the rack protrusions 34, 38 outward laterally, thereby forcing both wedges 26, 32 laterally from the central body 12. In the depicted embodiment, once in place in the spine, the teeth 22 will have secured the implant 10 to the bone to resist migration.

Figure 7:
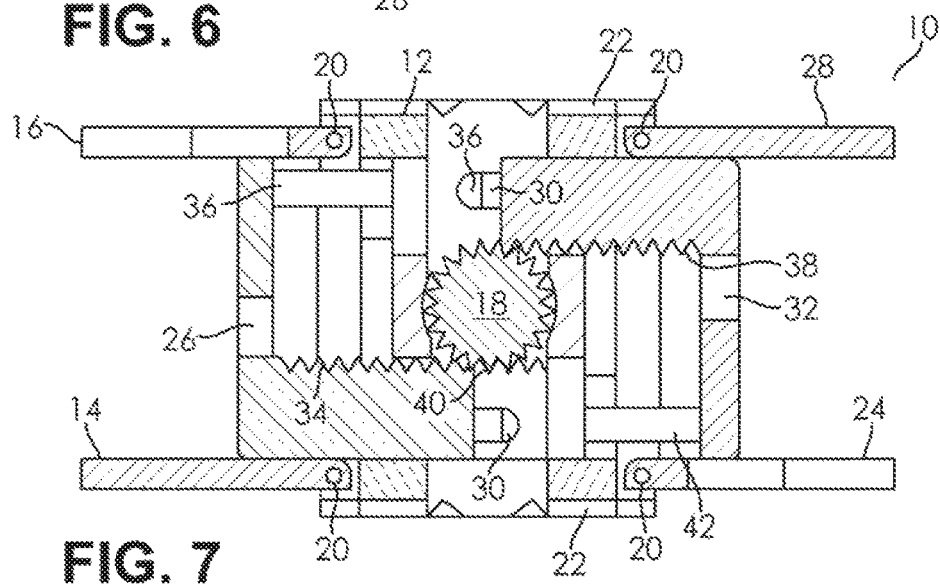
FIG. 7 depicts a rear sectional view of an exemplary spinal implant in an illustrative expanded configuration.

FIG. 7 depicts a rear sectional view of an exemplary spinal implant in an illustrative expanded configuration. In FIG. 7, the wedges 26 and 32 are driven outward from the central body 12 by the rack protrusions 34 and 38 engaged by the gear 40 to the rotatable drive shaft 18. In the depicted embodiment, the implant 10 was inserted between two vertebrae while in an unexpanded configuration, and the drive shaft 18 turned, as depicted in FIG. 1. In the illustrated embodiment, the wedges 26 and 32 have extended laterally, engaging their respective pairs of the four wings 14, 16, 24, 28. In the illustrated embodiment, the left wedge 26 forced the lower left wing 14 to swing about hinge pin 20 pair downward and outward. At the same time, in the depicted embodiment, the left wedge 26 forced the upper left wing 16 to swing about the hinge pin 20 pair upward and outward. In a similar manner, in the illustrated embodiment, the right wedge 32 forced the lower right wing 24 to swing about hinge pin 20 pair downward and outward. At the same time, in the depicted embodiment, the right wedge 32 forced the upper right wing 28 to swing about the hinge pin 20 pair upward and outward. In the illustrated embodiment, the lateral extension of the wedges 26 and 32 continued, driven by the rotation of drive shaft 18, until the wings 14, 16, 24, 28 are pressed against the vertebral endplates. In the depicted expanded embodiment configuration, the wings 14, 16, 24, 28 transmit load through the wedges 26, 32 to better stabilize the vertebral bodies.

Figure 8:
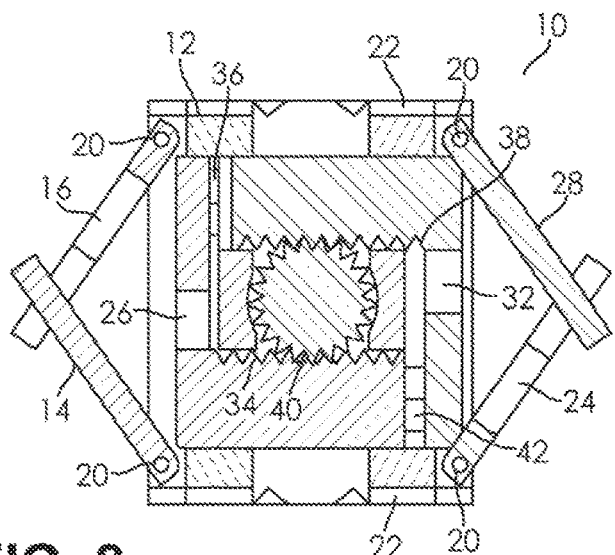
FIG. 8 depicts a rear sectional view of an exemplary spinal implant in an illustrative partially expanded configuration.

FIG. 8 depicts a rear sectional view of an exemplary spinal implant in an illustrative partially expanded configuration.

Figure 9:
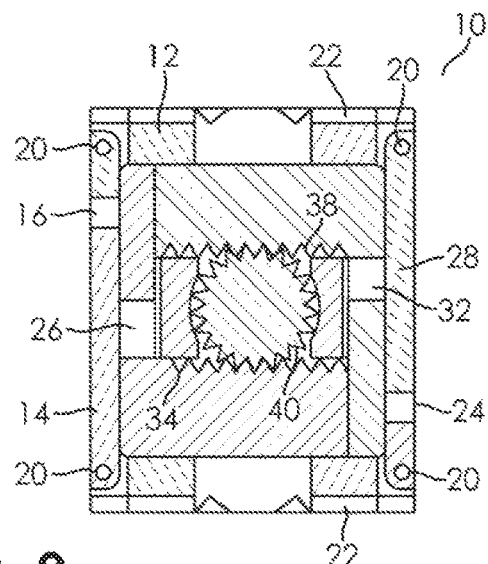
FIG. 9 depicts a rear sectional view of an exemplary spinal implant in an illustrative unexpanded configuration.

FIG. 9 depicts a rear sectional view of an exemplary spinal implant in an illustrative unexpanded configuration.

Figure 10:
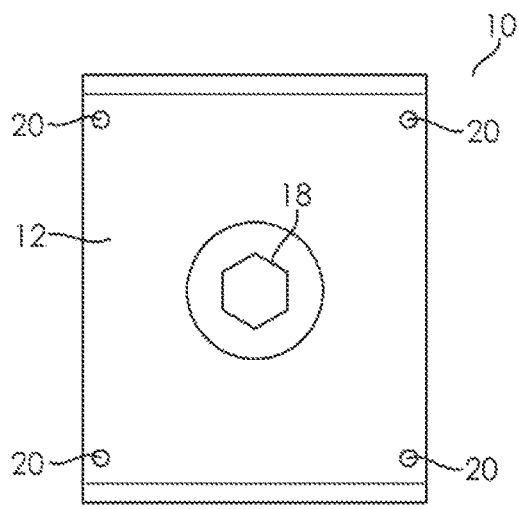
FIG. 10 depicts a rear view of an exemplary spinal implant in an illustrative unexpanded configuration.

FIG. 10 depicts a rear view of an exemplary spinal implant in an illustrative unexpanded configuration.

Figure 11:
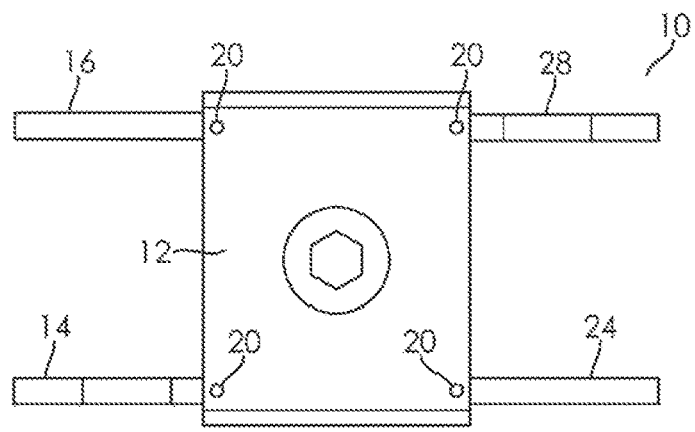
FIG. 11 depicts a rear view of an exemplary spinal implant in an illustrative expanded configuration.

FIG. 11 depicts a rear view of an exemplary spinal implant in an illustrative expanded configuration.

Figure 12:
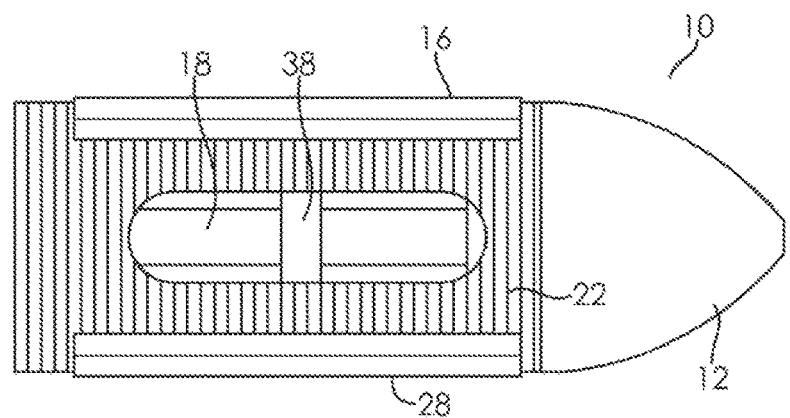
FIG. 12 depicts a top view of an exemplary spinal implant in an illustrative unexpanded configuration.

FIG. 12 depicts a top view of an exemplary spinal implant in an illustrative unexpanded configuration.

Figure 13:
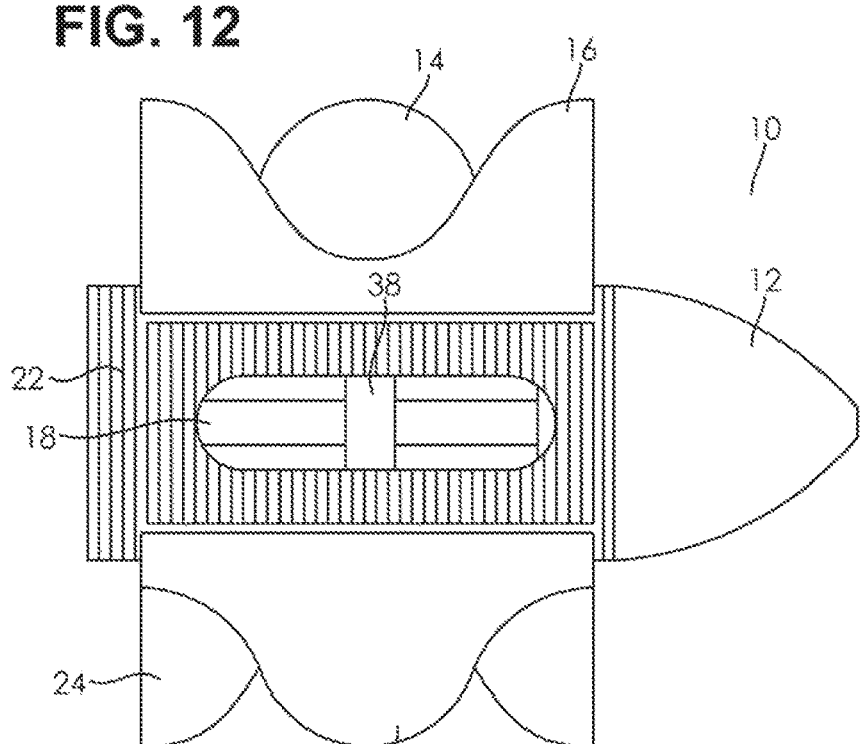
FIG. 13 depicts a top view of an exemplary spinal implant in an illustrative expanded configuration.

FIG. 13 depicts a top view of an exemplary spinal implant in an illustrative expanded configuration. In the depicted embodiment, the substantially arcuate shapes of the wings 14, 16, 24, 28 are visible. In some scenarios, the substantially arcuate shapes of the wings 14, 16, 24, 28 may approximate the shapes of vertebral body surfaces, increasing the spinal implant 10 surface area in contact with the vertebral bodies and reducing the load per unit area on the vertebrae. In the illustrated embodiment, when in an expanded configuration and installed between vertebrae, each of the wings 14, 16, 24, 28 operate in mechanical opposition to another wing to improve stabilization of the vertebral bodies. For example, the lower left wing 14 opposes the upper right wing 28, and, the lower right wing 24 opposes the upper right wing 28, strengthening the spinal implant 10 installation against rotational instability within the vertebrae 125.

Figure 14:
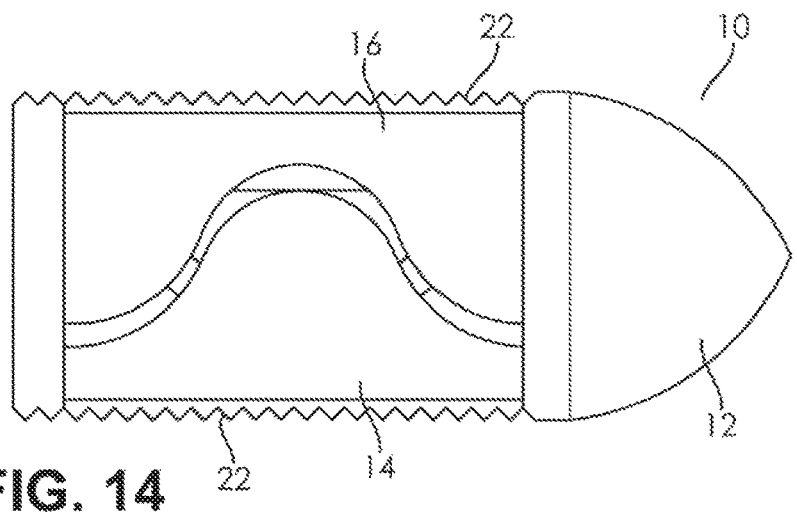
FIG. 14 depicts a side view of an exemplary spinal implant in an illustrative unexpanded configuration.

FIG. 14 depicts a side view of an exemplary spinal implant in an illustrative unexpanded configuration.

Figure 15:
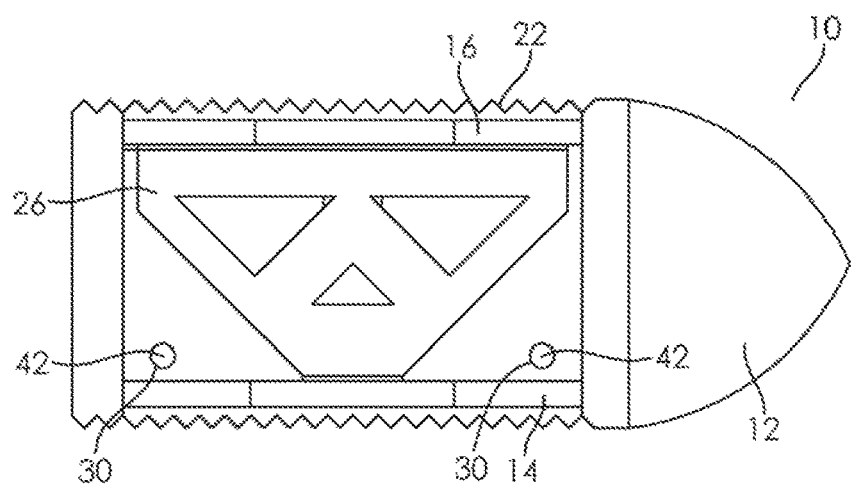
FIG. 15 depicts a side view of an exemplary spinal implant in an illustrative expanded configuration.

FIG. 15 depicts a side view of an exemplary spinal implant in an illustrative expanded configuration.

Figure 16:
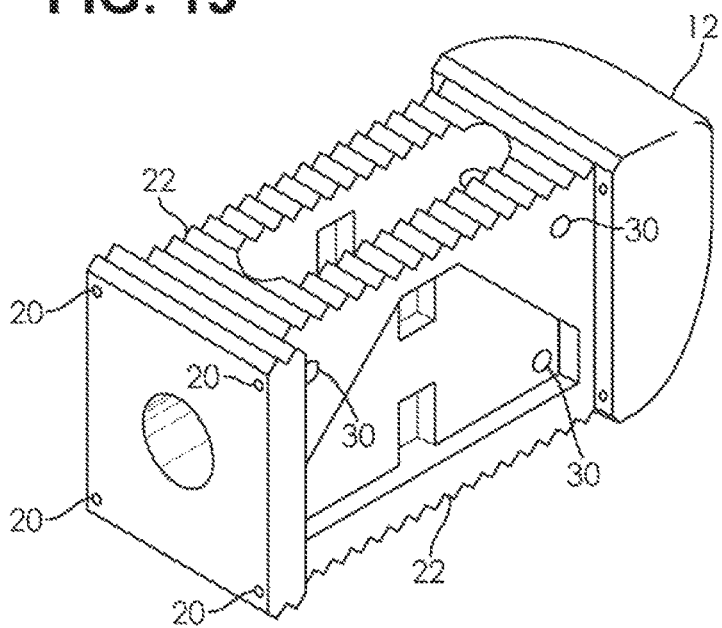
FIG. 16 depicts a side perspective view of an exemplary spinal implant central body.

FIG. 16 depicts a side perspective view of an exemplary spinal implant central body.

Figure 17:
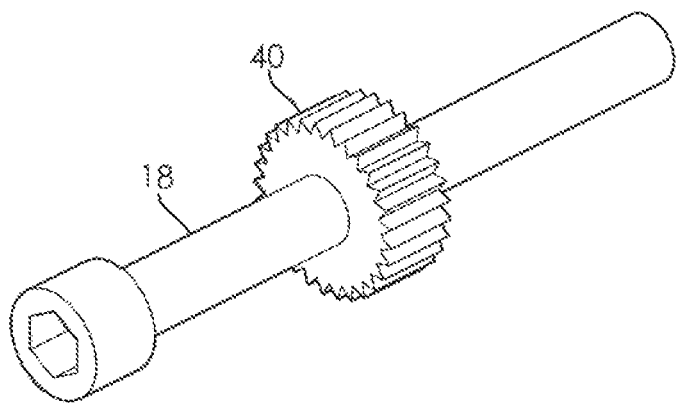
FIG. 17 depicts a perspective view of an exemplary spinal implant drive shaft.

FIG. 17 depicts a perspective view of an exemplary spinal implant drive shaft.

Figure 18:
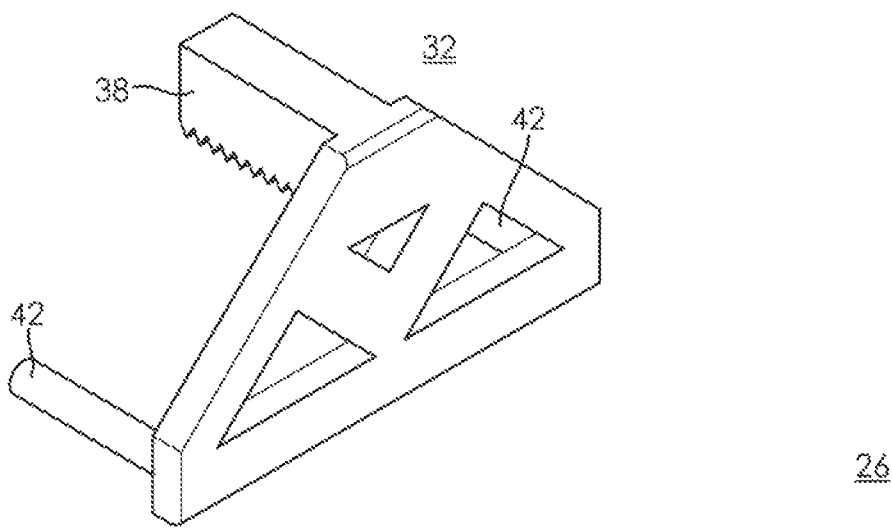
FIG. 18 depicts a front perspective view of an exemplary spinal implant wedge.

FIG. 18 depicts a front perspective view of an exemplary spinal implant wedge. In FIG. 18, the depicted spinal implant 10 right wedge 32 is configured with right guide protrusions 42 and right rack protrusion 38.

Figure 19:
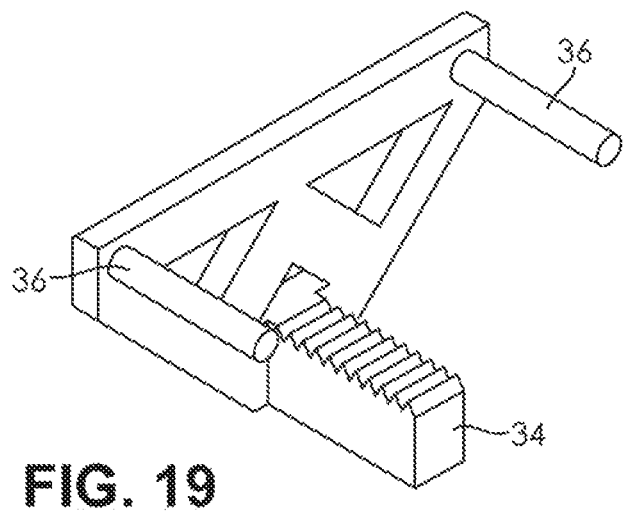
FIG. 19 depicts a rear perspective view of an exemplary spinal implant wedge.

FIG. 19 depicts a rear perspective view of an exemplary spinal implant wedge. In FIG. 19, the depicted spinal implant 10 left wedge 26 is configured with left guide protrusions 36 and left rack protrusion 34.

FIG. 20 depicts a perspective view of an exemplary spinal implant wing. In FIG. 20, the upper left wing 16 is configured with an integral hinge bushing 51 pair adapted to allow the wing to swing along a hinge axis bisecting the integral hinge bushing 51 pair.

FIG. 21 depicts a perspective view of an exemplary spinal implant wing. In FIG. 21, the lower right wing 24 is configured with an integral hinge bushing 51 pair adapted to allow the wing to swing along a hinge axis bisecting the integral hinge bushing 51 pair.

FIG. 22 depicts a perspective view of an exemplary spinal implant wing. In FIG. 22, the upper right wing 28 is configured with an integral hinge bushing 51 pair adapted to allow the wing to swing along a hinge axis bisecting the integral hinge bushing 51 pair.

FIG. 23 depicts a perspective view of an exemplary spinal implant wing. In FIG. 23, the lower left wing 14 is configured with an integral hinge bushing 51 pair adapted to allow the wing to swing along a hinge axis bisecting the integral hinge bushing 51 pair.

Although various embodiments have been described with reference to the Figures, other embodiments are possible. For example, in some embodiments, a laterally expandable spinal implant includes a central body with two wedges that are adapted to be received within inner guides on the central body. In various implementations, the wedges may have guide tabs that fit into holes in the central body. In some designs, Additionally, the wedges may have a rack that also extends into a chamber in the central body. In various embodiments, the central body may have a chamber extending axially through its center. In an illustrative example, the central chamber may house a shaft and gear. In some designs, the gear housed in the central chamber may mesh with the racks of the wedges. In various embodiments, the gear may force the wedges out laterally, as the gear turns. In some embodiments, four wings may be mounted axially in the corners of the central housing and allowed to swing in a hinge method. In some designs, the wedges may extend laterally, pushing the wings outward. In various implementations, the wings may pivot in a manner to allow them to move from the side walls of the central body until they press against the vertebral endplates superior and inferior.

Embodiments of the present invention generally concern spinal implants and more specifically, but not exclusively, concerns a laterally expandable vertebral implant. In various scenarios, a major cause of persistent, often disabling, back pain can arise by disruption of the disc annulus, chronic inflammation of the disc, or relative instability of the vertebral bodies surrounding a given disc, such as might occur due to a degenerative disease. In the more severe cases, some form of mechanical limitation to the movement of the vertebrae on either side of the subject disc is necessary. In such cases, the disc tissue is irreparably damaged, thereby necessitating removal of the entire disc. However, when the disc nucleus is removed without subsequent stabilization, the same disabling back pain often reoccurs due to persistent inflammation and/or instability.

In various scenarios exemplary of prior art spinal implant usage, various approaches have been developed to stabilize the adjacent vertebral bodies following excision of this material. For example, in one exemplary prior art approach, two adjacent vertebrae are fused together through a fusion device that is implanted between the vertebrae. Some of these existing implant designs have drawbacks that lower the spinal fusion rates. In some scenarios, these design drawbacks include flaws such that the implants subside into the vertebral endplates, thereby reducing the spacing between the vertebral bodies. In some scenarios exemplary of prior art fusion devices, and even some prosthetic devices, a large portion of the load is placed against the weakest part of the vertebral body which can lead to cavitation of the device into the surrounding vertebral endplates with subsequent collapse of the inner discal space and even damage of the vertebrae itself. Another frequent cause for subsidence related to usage of prior art fusion devices is created by having a small area of contact between the implant and the endplates. As one should appreciate, the less surface area of contact between the implant and the endplates, the greater the risk of subsidence.

Another flaw exemplary of prior art implant usage is the lack of stability created after implantation. Stability is crucial to the success of a fusion. The implant must be securely fixated to the vertebral bodies in order to ensure that no movement occurs between the two. If movement does occur between the vertebral bodies and implant, the bone may not properly fuse, thereby creating stability problems. Moreover, some designs exemplary of prior art implants limit the amount of graft material, which may be able to be used with the implant. The larger area of graft material that is able to contact the endplates, the better chances of a good, solid bone growth between the two vertebrae.

Some prior art implant designs have created implants in which the majority of the implant is positioned over the harder cortical bone of the apophyseal ring of the vertebrae in order to reduce the chances of subsidence. However, with such prior art implant designs, the implant is made from multiple separate components that are individually assembled together within the disc space. As should be appreciated, assembling such an implant in the disc space can be rather difficult. Such prior art implants also tend to lack a stiff central body, which is essential to the stability of the implant as well as the entire fusion construct.

In some scenarios exemplary of prior art spinal implant usage, some prior art devices may have the ability to expand laterally by having certain components slide out from a central body. While such prior art devices may increase the amount of surface contact area, the process itself can be difficult, and even damaging, as there is generally an extreme load placed upon the implant by the vertebral endplates. Although such an extreme load may help keep such a prior art implant in the desired location, and is often required to maintain the implant's positioning, it can also make it difficult to mechanically expand an implant inside the disc space. As such, these forces exerted on the sliding component can greatly resist the movement. Additionally, as these components slide against the face of the vertebral endplates, they can crack or break the fragile structure.

While multiple embodiments are disclosed, still other embodiments of the present invention will become apparent to those skilled in the art from this detailed description. The invention is capable of myriad modifications in various obvious aspects, all without departing from the spirit and scope of the present invention. In particular, it is noted that the respective features of various embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting. In the present disclosure, all embodiments where "comprising" is used may have as alternatives "consisting essentially of," or "consisting of." In the present disclosure, any method or apparatus embodiment may be devoid of one or more process steps or components. In the present disclosure, embodiments employing negative limitations are expressly disclosed and considered a part of this disclosure. Accordingly, the drawings and descriptions are to be regarded as illustrative in nature and not restrictive.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

Many suitable methods and corresponding materials to make each of the individual parts of embodiment apparatus are known in the art. According to an embodiment of the present invention, one or more of the parts may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as described herein-above may be used. Many suitable materials are known and available and can be selected and mixed depending on desired strength and flexibility, preferred manufacturing method and particular use, as will be apparent to a person of ordinary skill in the art.

In the present disclosure, various features are described as being optional, for example, through the use of the verb "may;", or, through the use of any of the phrases: "in some embodiments," "in some implementations," "in some designs," "in various embodiments," "in various implementations,", "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features, or with all three of the three possible features.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

In the present disclosure, expressions in parentheses may be understood as being optional. As used in the present disclosure, quotation marks may emphasize that the expression in quotation marks may also be understood in a figurative sense. As used in the present disclosure, quotation marks may identify a particular expression under discussion.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. An apparatus, comprising:
a spinal implant module, comprising:
a first pair of wings on one lateral side of the spinal implant module and a second pair of wings on an opposite lateral side of the spinal implant module;
a central body, comprising a substantially elongated structure configured to house the first and second pair of wings, wherein each pair of wings has a retracted position with the pair of wings folded flat against the central body and an extended position with the pair of wings extending perpendicular from the central body; and,
a drive shaft, rotatably retained within the central body, and configured rotate each pair of wings between the retracted and the extended position, wherein the extended position creates a larger surface contact area between the spinal implant module and vertebral bodies between which the spinal implant module is implanted.

2. The apparatus of claim 1, wherein each pair of wings comprises a first wing and a second wing each having a first edge pivotally connected to the central body and a second edge opposite the first edge.

3. The apparatus of claim 2, wherein the first and second wing each pivot outward from the central body along the first edge such that the second edge of the first wing moves away from the second edge of the second wing as the pair of wings rotate to the extended position.

4. The apparatus of claim 2, wherein the second edge of the first wing has an arcuate shape that corresponds to an arcuate shape of the second edge of the second wing to enable the pair of wings be flat against the central body in the retracted position.

5. The apparatus of claim 1, wherein the drive shaft further comprises a gear disposed along at least a portion of the drive shaft.

6. The apparatus of claim 5, further comprising a wedge corresponding to each pair of wings, wherein each wedge is slidably housed within the central body and in mechanical contact with one of the pair of wings.

7. The apparatus of claim 6, wherein the wedge engages with the gear to drive the pair of wings outward from the retracted position to the extended position when sufficient angular displacement is applied to the drive shaft.

8. The apparatus of claim 7, wherein the wedge further comprises a protrusion adapted to align the wedge with the central body.

9. The apparatus of claim 1, wherein the central body further comprises teeth.

10. An apparatus, comprising:
a spinal implant module, comprising:
a pair of wings on each lateral side of the spinal implant module, each of the pair of wings configured to be rotated between a retracted position and an extended position, wherein the extended position increases a top and bottom surface area of the spinal implant module to stabilize vertebral bodies between which the spinal implant module is implanted;
a central body, comprising a substantially elongated structure adapted to house each of the pair of wings in a retracted position flat against the lateral side of the central body, the central body configured with teeth disposed along a face of the central body; and,
a drive shaft, rotatably retained within the central body, and configured to secure the spinal implant module with stabilizing force applied to the vertebral bodies by the pairs of wings when inserted between vertebrae and sufficient angular displacement is applied to the drive shaft.

11. The apparatus of claim 10, wherein each pair of wings comprises a first wing and a second wing each having a first edge pivotally connected to the central body and a second edge opposite the first edge.

12. The apparatus of claim 11, wherein the first and second wing each pivot outward from the central body along the first edge such that the second edge of the first wing moves away from the second edge of the second wing as the pair of wings rotate to the extended position.

13. The apparatus of claim 10, wherein the drive shaft further comprises a gear disposed along at least a portion of the drive shaft.

14. The apparatus of claim 13, further comprising a wedge corresponding to each pair of wings, wherein each wedge is slidably housed within the central body and in mechanical contact with one of the pair of wings.

15. The apparatus of claim 14, wherein the wedge engages with the gear to drive the pair of wings outward from the retracted position to the extended position when sufficient angular displacement is applied to the drive shaft.

16. The apparatus of claim 15, wherein the wedge further comprises a protrusion adapted to align the wedge with the central body.

17. An apparatus, comprising:
a spinal implant module, comprising:
a pair of wings on each lateral side of the spinal implant module, each wing of each of the pair of wings having a substantially arcuate shape, the wings adapted to be rotated to an extended position to increase top and bottom surface area of the spinal implant module and stabilize vertebral bodies in between which the spinal implant module is implanted;
a central body, comprising a substantially elongated structure configured to house each of the pair of wings in a retracted position flat against the lateral side of the central body, the central body configured with teeth disposed along a face of the central body;
two wedges, slidably housed within the central body, each wedge in mechanical contact with one of the pairs wings and configured to slide outward from the central body to move the pair of wings to the extended position; and,
a drive shaft, rotatably retained within the central body, and configured to secure the spinal implant module with stabilizing force applied to the vertebral bodies by the pairs of wings when inserted between vertebrae and sufficient angular displacement is applied to the drive shaft.

18. The apparatus of claim 17, wherein the drive shaft further comprises a gear disposed along at least a portion of the drive shaft.

19. The apparatus of claim 17, wherein at least one wedge of the two wedges further comprises a protrusion adapted to align the at least one wedge with the central body.

20. The apparatus of claim 17, wherein each of the wedges engages with the gear to drive the wings outward into the extended position when sufficient angular displacement is applied to the drive shaft.

* * * * *